US006866782B2

(12) United States Patent
Scapol et al.

(10) Patent No.: US 6,866,782 B2
(45) Date of Patent: Mar. 15, 2005

(54) PROCESS FOR THE PURIFICATION OF PHARMACOLOGICALLY ACTIVE PROTEINS THROUGH CATIONIC EXCHANGE CHROMATOGRAPHY

(75) Inventors: Lucia Scapol, Sasso Marconi (IT); Giuseppe Claudio Viscomi, Sasso Marconi (IT)

(73) Assignee: Alfa Wassermann S.p.A., Alanno Scalo (IT)

( * ) Notice: Subject to any disclaimer, the term of this patent is extended or adjusted under 35 U.S.C. 154(b) by 0 days.

(21) Appl. No.: 10/166,459

(22) Filed: Jun. 10, 2002

(65) Prior Publication Data

US 2003/0010715 A1 Jan. 16, 2003

(30) Foreign Application Priority Data

Jul. 6, 2001 (IT) .................................. BO2001A0426

(51) Int. Cl.⁷ .............................................. B01D 15/08
(52) U.S. Cl. ....................... 210/635; 210/656; 424/85.4; 424/85.5; 424/85.6; 424/85.7; 530/351; 530/413; 530/416; 435/811
(58) Field of Search ................................ 210/635, 656, 210/659, 198.2; 424/85.4, 85.5, 85.6, 85.7; 530/351, 413, 416; 435/803, 811

(56) References Cited

U.S. PATENT DOCUMENTS

| | | | | |
|---|---|---|---|---|
| 4,228,154 A | * | 10/1980 | Fisher et al. ................. 530/364 |
| 4,732,683 A | * | 3/1988 | Georgiades et al. ........ 210/635 |
| 4,765,903 A | * | 8/1988 | D'Andrea et al. .......... 210/635 |
| 5,037,644 A | * | 8/1991 | Shaked et al. ............. 424/85.2 |
| 5,250,662 A | * | 10/1993 | Chang ........................ 530/364 |
| 5,367,054 A | * | 11/1994 | Lee ............................ 530/359 |
| 5,378,365 A | * | 1/1995 | Arrighi et al. .............. 210/635 |
| 5,486,470 A | * | 1/1996 | Darke et al. ................. 435/219 |
| 5,521,287 A | * | 5/1996 | Ohmura et al. ............. 530/363 |
| 5,616,691 A | * | 4/1997 | Takahashi et al. .......... 530/364 |
| 5,962,649 A | | 10/1999 | Noda et al. ................. 530/416 |
| 6,034,221 A | * | 3/2000 | Berezenko et al. ......... 530/362 |
| 6,150,504 A | * | 11/2000 | Van Der Laken et al. .. 530/364 |

FOREIGN PATENT DOCUMENTS

| | | | | |
|---|---|---|---|---|
| EP | 0 108 585 B1 | 5/1989 | ................. 530/416 |
| EP | 0 679 718 B1 | 9/2001 | ................. 530/416 |
| JP | WO 86/04067 | 7/1986 | ................. 530/416 |

OTHER PUBLICATIONS

Thatcher, Methods of Enzymol. 119, 166–177 (1986).*
"Isolation by gel–permeation chromatography of a non–covalent complex of Cibacron Blue F3G–A with human serum albumin" by: Anna Compagnini, Salvatore Fisichella, Salvatore Foti, Giuseppina Maccarrone, Rosaria Saletti; Journal of Chromatography A, 736 (1996) 115–123.

(List continued on next page.)

*Primary Examiner*—Ernest G. Therkorn
(74) *Attorney, Agent, or Firm*—Bucknam and Archer

(57) ABSTRACT

There is disclosed a process for the purification of pharmacologically active proteins based on the use of the cationic exchange chromatography on a solid matrix carried out at a more basic pH, i.e. higher, in respect of the pH corresponding to the isoelectric point, pI, of the proteins to be purified, pH at which however said proteins still remain absorbed. Buffer solutions with values of pH and of ionic strength adjusted from time to time to the kind of pharmacologically active protein to be purified are used in order to obtain such a result. The process is mainly addressed to the purification of the interferon and albumin proteins.

7 Claims, 4 Drawing Sheets

OTHER PUBLICATIONS

"Interferon from 1981 to 1986" by: Sidney Pestka; pp. 3–15 (inclusive), undated.

"Production of interferon–α in high cell density cultures of recombinant *Escherichia coli* and its single step purification from refolded inclusion body proteins" by K.R. Babu, S. Swaminathan, S. Marten, N. Khanna, and U. Rinas; Appl. Microbiol Biotechnol (2000) 53:655–660.

"Ion Exchange Chromatography for the Purification of Recombinant Human Alpha–2B Interferon, Comparative Study of Medium and High Resolution Gels" by: Rebeca Bouyón, José R. Hernández, Tania Aleaga, Hector Santana, Miriela Gil, Raudel Sosa, Yai Cruz, Alberto Agraz, and Luis Herrera; Biotechnologia Aplicada 1997; 14:189–192.

"Ion–Exchange Chromatography of Proteins" by: Shuichi Yamamoto, Kazuhiro Nakanishi, and Ryuichi Matsuno; Chromatographic Science Series, vol. 43 pp. 27–30 and 298–304, undated.

"Chromatography of Complex Protein Mixtures" by: Fred E Regnier; Journal of Chromatography, 418 (1987) 115–143 Biomedial Applications.

"A Simple Method for Estimating Isoelectric Points" by: Lampson, G.P. et al, pp. 374–377, undated.

"Separation of Proteins of Nearly the Same Size but Having Different Isoelectric Points by Convective Electrophoresis" by: A.K. Kontturi, K. Kontturi, and M. Vuoristo; Acta Chemica Scandinaica, 1996: 50: 102–106.

"Purification of Recombinant Human IFN–α2" by: David R. Thatcher and Nikos Panayotatos; Purification of Interferons pp. 166–177, undated.

"Electrophoretic transfer of proteins across polyacrylamide membranes" by: D.B. Rylatt, M. Napoli, D. Ogle, A. Gilbert, S. Lim, and C.H. Nair; Journal of Chromatography A, 865 (1999) 145–153.

"The Role of Protein Structure in Chromatographic Behavior" Article by: Fred E. Regnier (pp. 319–323), 1987.

"Large–Scale Production of Recombinant Proteins: Human Leukocyte Interferon" by: Fazal R. Khan and Vishva R. Rai; Hoffmann–La Roche, Inc., Nutley, NJ 161–169, inclusive, undated.

"Immobilized $Ni^{2+}$ –IDA Metal Chelating Affinity Membrane Chromatography for Purification of Commercial Human Serum Albumin" by: Yang Li, Jia Ling–yun, Zou Han–fa, Zhnag Yu–kui (National Chromatographic R & A Center, Dalian Institute of Chemical Physics, The Chinese Academy of Sciences, Dalian 116011)•Chinese Journal of Biotechnology, vol. 16 No. 1 Jan. 2000, pp 74–77.

"Purification of Recombinant Human Serum Albumin Efficient purification using STREAMLINE" by: Akinori Sumi, Kouzou Okuyama, Kaoru Kobayashi, Wataru Ohtani, Takao Ohmura, and Kazumasa Yokoyama; Bioseparation 8: 195–200, 1999.

"Expanded Bed Adsorption of Human Serum Albumin from Very Dense *Saccharomyces cerevesiae* Suspensions on Fluoride–Modified Zirconia" by: Ashim Mullick, Michael C. Flickinger, Biotechnol. Bioeng, 65(3), pp 282–290 (1999).

"Novel affinity separations based on perfluorocarbon emulsions Use of a perfluorocarbon affinity emulsion for the purification of human serum albumin from blood plasma in a fluidised bed" by: Graham E. McCreath, Howard A. Chase Duncan R. Purvis and Christopher R. Lowe; Journal Chromatography, 597 (1992) 189–196.

\* cited by examiner

PROCESS FOR THE PURIFICATION OF PHARMACOLOGICALLY ACTIVE PROTEINS THROUGH CATIONIC EXCHANGE CHROMATOGRAPHY

BACKGROUND OF THE INVENTION

A wide part of the biomedical sciences bases itself on the use of pharmacologically active proteins both of natural origin, obtained by means of extractive techniques, and of synthetic origin, obtained by means of techniques from recombinant DNA. The purity level of the interesting products is important in both cases, because the understanding of their activity is determined by the possibility of strictly binding the biological effect with the presence of a fixed amount of the protein.

In this context the purification processes of pharmacologically active proteins have gained an important part because the purity of the manufactured protein assumes remarkable significance when active principles or excipients contained in medicinal specialities are involved. The possibility of causing toxic effects and/or producing adverse effects during therapy have in fact pushed the authorities responsible for the registration and the authorization to the marketing of medicines based on proteins to introduce ever more stringent rules in order to determine the quality and the manufacturing consistency of active principles of proteic origin contained in marketed medicines.

From the above said the importance of the purification processes of the proteins clearly appears in which the main difficulty resides in the fact that the pharmacologically active proteins are always in composite mixtures together with many other proteins.

This fact is true both in the case natural sources are used for extracting the pharmacologically active protein, like for instance blood, extracts from animal or vegetal organs, and in the case recombinant DNA techniques are used because the proteins show chemical-physical properties similar between them independently from their origin.

Therefore from the above it comes that, in the case of purifications of pharmacologically active proteins, a protein mixed together with other proteins with similar properties and often abundantly exceeding the amount of the wanted protein has to be isolated with a high purity degree.

The task is exacting and several purification steps are normally used in order to gain the wanted purity levels. The purification processes become in this way very complex and the success of an industrial manufacturing of a protein is essentially bound to the efficiency of the purification process because this latter amply determines the manufacturing costs.

Many techniques are used for purifying proteins, like, for instance, selective precipitations in aqueous and organic solvents or with caotropic agents; separations by means of filtrations and/or dialysis; processes of immuno-precipitation with suitable antibodies; chromatographic processes.

These latter have gained in the recent years largely the greater importance mainly because they allow to get the requested purity degrees, as reported from Regnier F. E. on J. Chromatogr. 418, 115–143, (1987).

Many techniques are cited in the scientific literature and can be classified on the basis of the mechanism of action applied for separating the proteins like, for instance, separation on the basis of the molecular weight, absorption on polar matrices, also named normal stationary phases, absorption on non polar matrices, called reverse stationary phases, absorption by selective affinity with ligands bound to inert matrices, like heavy metals as copper, zinc, iron and platinum, chemical dyes like the brilliant blue, proteins like protein A and protein G, carbohydrates like the polysaccharides and the glucosaminoglycans, absorption by immuno-affinity with specific antibodies bound on inert matrices, absorption by ionic interaction with electrostatically charged ligands bound on inert matrices.

The selectivity, i.e. the capability to selectively recognize the wanted protein, the cost and the possibility to be used at industrial level are used as parameters to evaluate the performances of the different chromatographic techniques.

On the basis of these parameters, the immuno-affinity chromatography is considered that which warrants the greater selectivity, but it shows drawbacks like high costs of use, risks of denaturation of the antibody and risks connected to the end safety of the purified product because the antibody is of animal origin.

The chromatography which uses the ionic interaction, also called ionic exchange chromatography, is considered the less risky technique for keeping the pharmacological activity of the proteins and the easier to be carried out in industrial manner with low costs of management but it shows the drawback to be poorly selective.

Therefore it would be very advantageous to find conditions of execution of a ionic exchange chromatography that increase its selectivity so that to make it competitive with the other techniques from the point of view of the purity of the obtained product.

The ionic exchange chromatography is usually carried out by using columns of various sizes, filled with solid matrices containing chemical groups which, permanently or under particular conditions, are electrostatically charged.

A compound put into an ionic exchange column interacts by means of a coulomb attraction/repulsion with the charges bound to the matrix. Different compounds contained in a mixture will be able to bind themselves to the stationary phase in function of the amount of the possessed charge, and consequently they will be kept more or less, so defining their separation at the column exit.

The chromatography is named cationic exchange chromatography when the charges of the matrix are negative, because the cations are kept, while it is named anionic exchange chromatography when the charges of the matrix are positive.

The proteins are compounds having high molecular weight, higher than 10,000 Daltons, made by heterogeneous polymers of aminoacids; some aminoacids have in their side chain functional groups that can be ionized in function of the pH of the solution in negative manner, acidic aminoacids, or in positive manner, basic aminoacids, and therefore all the proteins possess a great number of negative and positive charges. The isoelectric point, pI, of a protein is the pH at which the protein is neutral because the contribution of the negative charges is equal to that of the positive charges, a protein put in an electronic field at pI is not attracted from any of the polarities of the electric field.

The number of the negative charges increases at pH higher than pI and the protein gains a net negative charge while the opposite happens at pH lower than pI and the protein gains a net positive charge. Every protein has its own characteristic pI which distinguishes it from the others and some proteins tend to become insoluble at the isoelectric point.

When a protein is in a solution at a pH lower than pI it has a net positive charge and therefore can interact with a negatively charged matrix and can be submitted to a cationic exchange chromatography while the protein can be submitted to an anionic exchange chromatography at pH higher than its pI, as reported from Regnier F. E., Science, 238, 319–323, (1987) and from Yamamoto S. et al., Chromatographic Science Series, 43, (1988), Marcel Dekker, Inc. Publisher, New York.

On the contrary we have unexpectedly found, and on this fact the object of the present invention bases itself, that it is possible to find a range of pH values higher than the corresponding pI of the protein at which pH the proteins still stay absorbed on matrices of cationic exchange chromatography so that it is still possible to carry out cationic exchange chromatographies. Such a situation is particularly important because a high selectivity between the proteins is gained under these conditions because also very small differences of pI between proteins become enough in order to get significant separations so affording a high efficiency of purification.

This latter aspect is particularly important in the purification processes of recombinant proteins wherein the wanted product is often accompanied from correlated impurities, i.e. made from very small structural changes of the product, like, for instance, different oxidation states, acetylations, loss of amidic functions and so on. This kind of impurities is very difficult to clear away also by means of immuno-affinity chromatographies because in most cases the antibodies are not able to distinguish them.

The mechanism which can explain the found phenomenon bases itself on the fact that the distribution of the charges along the external surface of the proteins is not uniform so that also when the pH is little higher than pI and the protein has a total net negative charge, there are still some positive charges located into the molecule than can interact with a negative stationary phase.

In order to make effective this mechanism it is important that the excess of negative charges is not too much accentuated otherwise the electric fields created from the negative charges would be so high as to prevent the interaction of the whole protein with the negatively charged chromatographic matrix.

Moreover its is necessary that the ionic strength of the solutions used as eluents is suitably controlled because a high ionic strength would have the effect of shielding the protein so preventing its interaction with the stationary phase.

Lampson G. P. et al., Anal. Biochem., 11, 374–377, (1965), in confirmation report the case of proteins like human gamma globulin, ribonuclease, hemoglobin, delta chymotrypsin, globin and lysozyme in which making small pH variations but keeping a too much high ionic strength, given by a 0.1 M phosphates solution, the elution in cationic exchange chromatographies happened at a pH of almost 0.4 unites lower than pI.

The above mentioned principle, on which the present invention bases itself, has never been used, to inventors' knowledge, in order to carry out efficient processes of purification of proteins.

The possibility of using differences of the isoelectric point of proteins in order to optimize the purification processes described by Kontturi A. K. et al., Acta Chem. Scand., 50 (2), 102–106, (1996) in fact refers to a conventional use of the ionic exchange chromatography wherein the cationic exchange chromatography is always carried out at a pH lower than the isoelectric point while the anionic exchange chromatography is carried out at a pH higher than the isoelectric point. The process described in the present patent application is such that the cationic exchange chromatographies are on the contrary carried out at a pH higher than the isoelectric point of the protein.

The process described in the present patent application can be considered of general nature as shown in the reported examples wherein it has been demonstrated how it is successfully applicable both to a protein of natural origin and to a protein from recombinant DNA. The difference between protein and protein is in the extent of the range of the field of the pH, higher than pI, useful for the purification of the interesting protein. In fact, for instance, as it will be shown in the following examples, such range is of about 0.2 pH units in the case of the interferon proteins while it is of about one pH unit in the case of albumin.

The application of the present invention to the purification of a recombinant alpha interferon (rIFNα) whose isoelectric point is 5.9, as reported from Thatcher D. and Panayotatos N., Methods Enzymol. 119, 166–177, (1986), will be reported among the examples and it will be shown how it is possible and advantageous to purify it in cationic exchange at a pH of 6.1. Moreover the example will be shown of the human seric albumin whose pI is 4.9, as reported by Rylatt D. B. et al., J. Chromatogr., 865, 145–153, (1999), and it will be shown how it is possible and advantageous to purify it in cationic exchange at a pH of 6.0.

The advantages of the process object of the present invention are very remarkable if compared with the results of the processes described in scientific publications and/or patents directed to the purification of α interferon and of human seric albumin, processes that usually require three or more subsequent treatments, fact that causes a high industrial cost and a decrease of the yields.

Thatcher D. and Panayotatos N. describe the purification of the human recombinant alpha interferon rIFN-α2, Methods Enzymol., 119, 166–177, (1986) through five subsequent treatments: a) cationic exchange chromatography; b) anionic exchange chromatography; c) affinity chromatography for heavy metals; d) treatment with a saturated solution of ammonium sulphate; e) molecular exclusion chromatography.

European Patent 0108585 describes for the purification of the interferon the subsequent use of three types of chromatography: a) immuno-affinity; b) cationic exchange; c) molecular exclusion.

U.S. Pat. No. 4,765,903 on the interferon purification describes the sequential use of four types of chromatography: a) immuno-affinity with a monoclonal antibody; b) inverted phase; c) cationic exchange; d) molecular exclusion.

European Patent 0679718 describes a process for the alpha interferon production that envisages the following four chromatographic steps: a) metal-chelating; b) cationic exchange; c) anionic exchange; d) gel filtration.

Other publications and patents describe three or more treatments necessary for the purification of the interferon proteins, for instance U.S. Pat. No. 4,732,683, International Patent Application WO 8604067 and the publication from Khan F. R. and Rai V. R., Bioprocess Technol., 7, 161–169, (1990).

The quoted examples cover the most relevant matter reported about the purification of interferon in general and of alpha interferon in particular. They show how the purification of this latter is particularly difficult and requires many purification steps. Moreover it has to be underlined how high purification levels are in particular obtained by means of immuno-affinity chromatographies by using monoclonal antibodies of murine origin. However the presence of such a chromatographic technique within processes of industrial production aimed at manufacturing active principles for pharmaceutic use in humans causes the risk of possible viral contaminations from viruses of murine origin because of the presence of possible immunogenic fragments coming from the murine immunoglobulins in the end product and because of the difficulties to validate the chromatographic matrices from the industrial point of view.

Moreover from the briefly illustrated examples the cationic exchange chromatography results to be widely used but never as unique separative technique because its performances are limited with regards to the increase of the purity levels.

The publications from Babu K. R. et al., Appl. Microbiol. Biotechnol., 53 (6), 655–660, (2000) and Bouyon R. et al., Biotecnologia Aplicada 14, 189–192, (1997), describe purification processes of alpha interferon in one step by means of ionic exchange chromatography in saline gradient. However in both cases to get a product sufficiently pure the authors have to isolate only some of the chromatographic fractions in which the alpha interferon is contained so obtaining very low yields, until a 7.5% minimum. Moreover the described purification processes of chromatography in saline gradient are not apt to be used at industrial level.

Many techniques of chromatographic purification are described also in the case of the human albumin starting from preparations of albumin obtained by fractionating human serum or by means of techniques of recombinant DNA, techniques complex and scarcely transferable at industrial level that confirm how the problem of an effective purification of human albumin, both of natural and of recombinant origin, is still existing.

U.S. Pat. Nos. 6,150,504 and 5,521,287 describe the purification of the albumin by means of ionic exchange chromatography and hydrophobic interaction. The purification scheme described in U.S. Pat. No. 6,034,221 envisages the albumin purification by means of two chromatographic steps, one ultrafiltration process and two further steps of chromatographic purification.

Less conventional methods of albumin purification in which anionic exchange chromatographies in fluid bed or affinity-chromagraphies interacting with commercially available matrices like those of Streamline®, or suitably prepared, like particles of modified zirconium or emulsions of perfluoro hydrocarbons, are used, are described in U.S. Pat. No. 5,962,649 and in the publications from Sumi A. et al., Bioseparation, 8 (1–5), 195–200, (1999), Mullick A. and Flickinger M. C., Biotechnol. Bioeng., 65 (3), 282–290, (1999) and Mc Creath G. E. et al., J. Chromatogr., 597 (1–2), 189–196. (1992).

Lastly techniques of purification of albumin on heavy metals have also been described from Yang L. et al., Sheng Wu Kung Cheng Hsueh Pao, 16 (1), 74–77, (2000) and techniques of affinity on matrices to which molecules of dyes like Cibacron Blue F3G are bound have been described from Compagnini A. et al., J. Chromatogr. A, 736 (1–2), 115, (1996).

All these techniques show in various manner problems of complexity of realization and of high costs so that the problem of individuating new purification processes of pharmacologically active proteins both of easy and efficient industrial feasibility and economically advantageous is not resolved.

The invention below described gives an answer to these important requirements by providing a process for the purification of pharmacologically active proteins of easy industrial exploitation and of low cost with remarkable economical advantages.

DESCRIPTION OF THE INVENTION

Figure 1A:
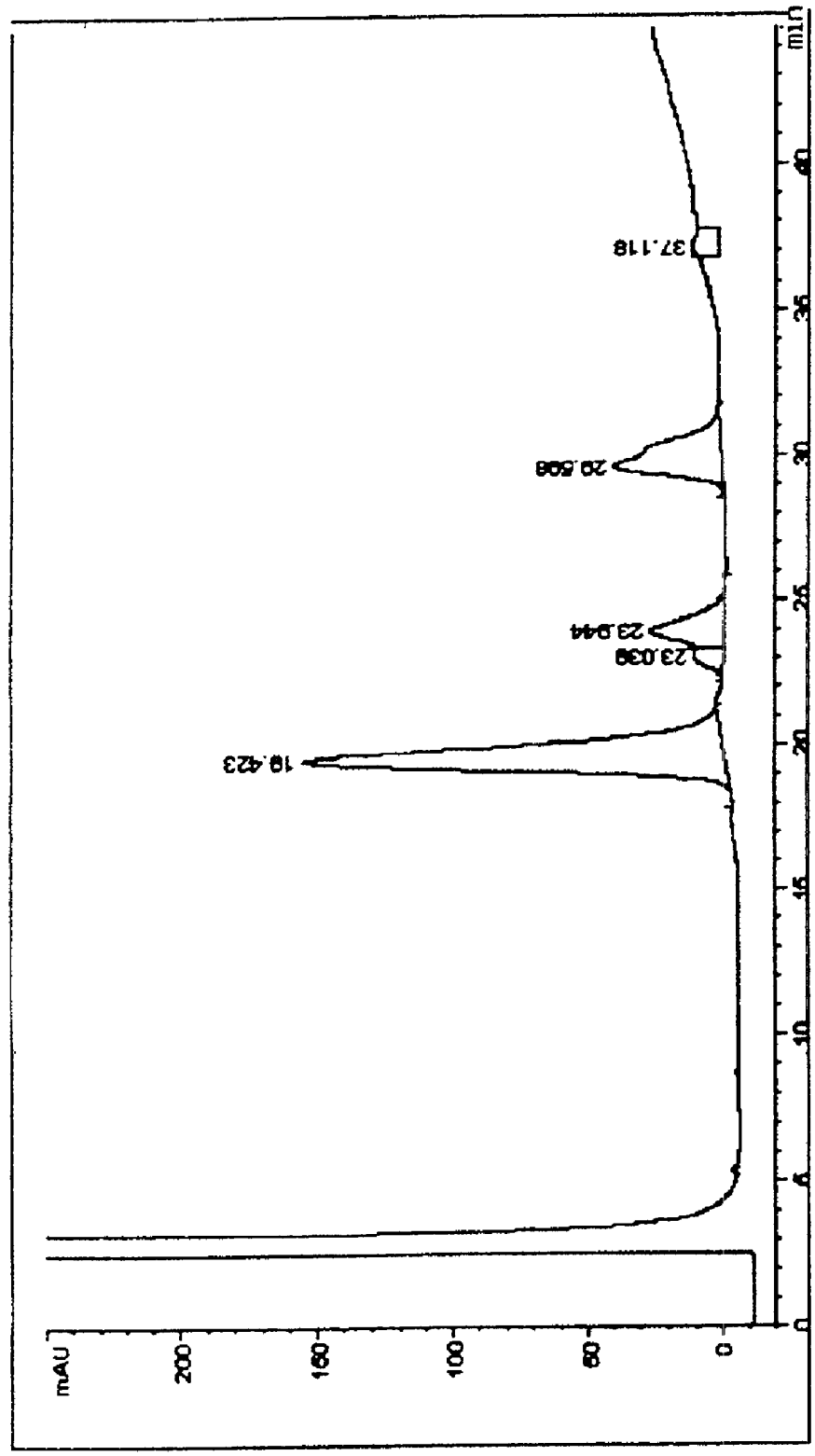
FIG. 1a show the chromatographic profile of the interferon solution before the purification and FIG. 1b the chromatographic profile after the purification.

The present invention refers to a process for the purification of pharmacologically active proteins based on the use of the cationic exchange chromatography on a solid matrix under peculiar conditions which comprise, after the loading of the sample, conditioning the column with eluents of suitable pH and ionic strength so that in the column is uniformly present a more basic pH, i.e. higher, than the corresponding isoelectric point, pI, of the pharmacologically active proteins, at which pH however said proteins stay still absorbed on the solid matrix used for the cationic exchange chromatography. After this phase of conditioning the pharmacologically active proteins are eluted from the column by increasing the ionic strength and/or the pH of the eluents.

The effective performance of the present invention requires the individuation of the right combination among the chromatographic matrix to be used, the pH value higher then then pI and the ionic strength to be used in the chromatographic eluents because, once defined the chromatographic matrix, efficient purifications can be obtained by making limited variations of pH and/or ionic strength often of tenths of pH units and/or of variations of ionic strength of few hundreds of $\mu$S.

All the functionalized solid matrices commonly used as stationary phases for cationic exchange chromatographies can be used, in particular however the stationary phases named strong cationic exchange have to be preferred when the pI of the protein to be purified is lower than 6 while stationary phases with cationic exchange both strong and weak can be used without exception for proteins having pI higher than 6. Said stationary phases may have siliceous or polymeric matrix, functionalized by means of sulfonic or carboxylic groups both under proton or alkaline salts form. Stationary phases commercially available like, for instance, Source® S (Pharmacia Biotech), Sepharose® SP-Fast Flow, Sepharose® SP-High Performance, Sp Sepharose® XL (Pharmacia Biotech), Fractogel® S (Merck, Darmstadt), Mustang® S (Pall Corporate), CM Sepharose® FF (Pharmacia Biotech), Dowex®, Bio-Rad® AG (Bio- Rad), Poros® S (PerSeptive Biosystems), Shodex® -S, Toyopearl® SP (Tosohass) can be successfully used.

The range of the pH values at which the present invention can efficiently be carried out is very wide, depending upon the isoelectric points of the pharmacologically active proteins that have to be purified, and is comprised between 2 and 11, preferably between 4 and 8.5.

The extension of the range of the pH values higher than pI within which the process described in the present invention is applicable can vary from pH values corresponding to the pI of the pharmacologically active proteins to one pH unit over said pI, showing remarkable differences from protein to protein.

For instance, it has been found that in the case of the recombinant alpha 2b interferon (rIFNα-2b) it is possible to obtain the absorption of the protein on a cationic exchange matrix till 0.2 pH units over its pI of 5.9 and consequently it is possible to carry out its purification by means of a cationic exchange chromatography while it has been found in the case of the human serum albumin that the protein stays absorbed till one pH unit over its pI.

The range of the saline concentrations of the aqueous solutions employed as efficiently usable eluents depends on the kind of pharmacologically active protein to be purified and it has been found comprised between values of 1 mM and 100 mM, preferably between 1 mM and 30 mM.

For instance, in the case of the purification of the recombinant alpha 2b interferon (rIFNα-2b) the concentration of the aqueous saline solutions is comprised between 1 mM and 30 mM, preferably between 5 and 15 mM.

The need to have fixed and stable pH values of the eluents used for the chromatographies object of the present invention makes very useful, even if not absolutely necessary, to employ aqueous solutions suitably buffered containing from 5 to 100 mM, preferably from 10 to 20 mM of buffered mixtures. Every chemical substance or mixture of chemical substances having a buffering power in the range of the pH between 2 and 11 can be advantageously employed because the pH values of the eluents that can be used are comprised between 2 and 11.

Many aqueous buffer solutions can be advantageously used in carrying out the present invention comprised those containing: glycine and sodium chloride, maleic acid and sodium hydroxide, malonic acid and sodium hydroxide, lactic acid and sodium hydroxide, formic acid and sodium or lithium hydroxide, succinic acid and sodium hydroxide, N-methylpiperazine and hydrochloric acid, piperazine and hydrochloric or acetic acid, L-hystidine and hydrochloric acid, 4-(2-hydroxyethyl)-1-piperazinethanesulfonic acid and sodium or lithium hydroxide, N-methyldiethanolamine and sulphuric acid, N-methyldiethanolamine and hydrochloric or acetic acid, pyridine and formic acid, dibasic sodium citrate and sodium hydroxide, monobasic potassium phthalate and hydrochloric acid, monobasic potassium phthalate and sodium hydroxide, monobasic potassium phosphate and dibasic sodium phosphate, bicine and sodium hydroxide, sodium barbital and hydrochloric acid, sodium borate and hydrochloric acid, sodium borate and sodium hydroxide, 1,3-diaminopropane and hydrochloric acid, citric acid and dibasic sodium phosphate, sodium acetate and acetic acid, imidazole and hydrochloric acid, triethanolamine and hydrochloric or acetic acid, tris(hydroxymethylaminomethane) and hydrochloric acid, sodium carbonate and sodium acid carbonate, ethanolamine and hydrochloric acid, piperidine and hydrochloric acid, trimethylamine and formic acid, pyridine and acetic acid, trimethylamine and acetic acid, trimethylamine and hydrochloric acid, ammonium hydroxide and formic acid, ammonium hydroxide and acetic acid, trimethylamine and sodium carbonate, ammonium carbonate and ammonium hydroxide.

In particular, in the case of the purification of the recombinant alpha 2b interferon (rIFNα-2b) all the buffer solutions that show a buffering power at the pH comprised between 5.9 and 6.1 can be used, preferably buffer solutions at pH between 5.9 and 6.1 containing monobasic potassium phosphate and dibasic sodium phosphate, monobasic potassium phthalate and sodium hydroxide, dibasic sodium citrate and sodium hydroxide, citric acid and dibasic sodium phosphate, imidazole and hydrochloric acid, while in the case of the purification of the human serum albumin buffer solutions can be used containing the same mixtures of chemical compounds showing a buffering power at the pH comprised between 4.9 and 6.0.

The aqueous solutions used as eluents can contain, in addition to the chemical substances used for buffering the pH, also chemical substances that have the task to modify the ionic strength of the solution. To this end both organic salts, such for instance carboxylates, alkylsulfonates, phthalates or inorganic salts, like for instance sulphates, chlorides, phosphates which can be salified with sodium, potassium, ammonium, primary, secondary, tertiary or aromatic amines, can be advantageously used.

These compounds can advantageously be used at a concentration comprised between values from 1 mM to 100 mM, preferably between 1 mM and 30 mM.

For instance, in the case of the purification of the recombinant alpha 2b interferon (rIFNα-2b) the concentration of these compounds can vary between 1 mM and 30 mM, preferably between 2 and 20 mM.

The efficiency of the purification can be increased, before the elution of the pharmacologically active proteins, by means of one or more washings carried out with eluents having suitable pH and ionic strength, so that the column is always at a pH higher than pI.

For instance, in the case of the human serum albumin whose pI is 4.9, washings can be carried out with buffer solutions at pH comprised between 5.5 and 5.8, while in the case of the recombinant alpha 2 b interferon (rIFNα-2b) whose pI is 5.9 washings can be carried out with buffer solutions at a pH comprised between 6.0 and 6.1.

The amount of eluent passed across during these washings is variable, normally comprised between 5 and 100 column volumes (CV).

For instance, in the case of the human serum albumin the washings executed are comprised between 20 and 40 CV while in the case of the recombinant alpha 2b interferon (rIFNα-2b) between 10 and 80 CV.

The amount of product to be purified that can be put in the column depends on the chromatographic matrices used, and can arrive until a maximum of 100 milligrams of total proteins for each milliliter of stationary phase even if usually lower amounts are used, comprised between 5 and 20 mg/ml.

The eluents can pass through the column at a linear speed compatible with the stationary phases until a maximum value equal to 10 cm/min.

The above illustrated purification process can be applied to all pharmacologically active proteins; the purification of the interferon proteins with particular regard to the interferons alpha, beta, gamma, delta, omega, tau, to the natural alpha interferon from leukocytes, to the recombinant alpha 2b and consensus interferons and the purification of the albumin with particular regard to the human albumin both of natural and recombinant origin are preferred in the execution of the present invention.

Scope of the above described purification process is to get in an industrial and economical manner pharmacologically active proteins at a purity degree such as to be directly used for the manufacturing of the medicinal specialities which contain them.

In particular, the medicinal specialities preferred within the scope of the present invention are those containing interferon, still more preferably recombinant alpha 2b interferon (rIFNα-2b), and albumin, still more preferably human albumin both of natural and recombinant origin.

Some illustrative examples of the process object of the present invention are reported hereinafter with the sole scope to make clearer the invention but they do not have to be considered in any way restrictive of the invention itself.

EXAMPLE 1
Production of the Recombinant Alpha 2b Interferon (rIFNα-2b)

A part of cells of the *Escherichia coli* BL21 DE3 strain has been transformed with 5 ng of the pET9a-IFNα-2b plasmid, obtained by cloning a synthetic gene reproducing the human gene sequence of IFNα-2b, suitably modified in order to apt the sequence to the codons more frequent in *Escherichia coli,* into the pET9a plasmid (Novagen).

The proteic sequence expressed from the *Escherichia coli* cells modified as above shown is equal to that reported in Methods in Enzymology, Interferons, part C, editor Pestka S., 119, 3–14, (1986), published from Academic Press Inc.

The *Escherichia coli* BL21 DE3 strain transformed by means of the pET9a-IFNα-2b plasmid has been put in culture in a flask in a suitable culture medium, for instance a solution containing 12 g/l of phytopeptone (Phyto peptoton, BBL), 24 g/l of yeast extracts (Yeast extract, DIFCO), 4 g/l of glycerol (BDH) and neomycin, at 37° C. for a time sufficient to arrive at a value of optical density at 600 nm equal to 0.6–0.8, usually 7–9 hours. The so obtained culture is then used at the dilution from 1 to 100 to inoculate a 5 l fermenter where a culture medium equal to that of the flask, previously described, was contained. The culture is kept 14 hours at 37° C. with a aeration equal to one air volume each minute in respect of the culture volume.

The bacterial cells are collected by centrifugation at 6000 rounds per minute (rpm) at the end of the culture, they are suspended in a suitable aqueous solution containing 1 mM of dithiothreitol (DTT) in amount not higher than 6 ml for each gram of wet weight of the bacterial centrifuged. The bacterial suspension is submitted to cell lysis by means of consolidated and described techniques, like for instance breaking by ultrasounds or by hydraulic pressure.

The resulting suspension is recovered by centrifugation and the solid part is suspended in a 50 ml saline solution containing 1 mM of DTT and again centrifuged.

The solid component, constituent the included bodies, is collected and suspended under vigorous stirring at room temperature into 450 ml of a solution containing 6M of guanidinium chloride, 50 mM of Tris-HCl at pH 8 and 0.1 mM of EDTA. The suspension is centrifuged and the supernatant is diluted in the ratio from 1 to 100 to 1 to 200 in a saline solution containing 50 mM of Tris-HCl at pH 8 and 0.1 mM of EDTA at pH 8 suitable for the renaturation of the protein. The solution for the renaturation can contain amino acids, like for instance glycine or arginine; mixtures of compounds containing sulfides in the oxidated and reduced form with the disulfide bridge formed, like for instance glutathione, ethanolamine, cysteine. The renaturation is carried out under vigorous stirring of the solution at 4° C. for almost 72 hours and then the solution is filtered and then concentrated by means of a process of dia-filtration versus a buffer made by 40 mM of Tris-HCl at pH 8 until an end concentration factor from 5 to 10 times. The end concentration of the solution is usually comprised between 0.4 and 1.0 mg/ml.

EXAMPLE 2
Purification of the Recombinant Alpha-2b Interferon (rIFNα-2b)

A 1M solution of sodium acetate is added until the 20 mM end concentration to the proteic mixture containing rIFNα-2b coming from example 1 and the mixture is brought to pH 5.5 with acetic acid. The so obtained solution is charged on a strong cationic exchange column containing the commercially available chromatographic matrix Mustang® S (Pall Corporate), a strong cation exchange medium consisting of a hydrophilic polymer with sulfonic acid groups crosslinked on a poly ether sulfone membrane. The cationic exchange column is conditioned, before the charge of the proteic solution, by means of a 20 mM sodium acetate solution at pH 5.5 in amount equal to 20 column volumes (CV).

The proteic solution is then charged at such amount that the 10 mg value of proteins charged for each milliliter of stationary phase is not exceeded, preferably in amounts comprised between 6 and 8 mg/ml.

After the charge, the products bound to the stationary phase are submitted to a first cycle of washing by means of a saline solution at pH 6.1 made by a mixture of monobasic potassium phosphate and dibasic sodium phosphate at an overall concentration comprised between 5 and 15 mM. The optimum concentration of the solution is anyway fixed by the fact that the conductivity has not to exceed about 1800 $\mu$S. A total amount of solution comprised between 5 and 60 CV, preferably between 25 and 35 CV, is used.

A second cycle of washing is then carried out by using the same solution of the first cycle of washing to which an amount of potassium chloride is added equal to an end concentration not exceeding 3 mM, preferably 2 mM; a total amount of solution comprised between 10 and 100 CV, preferably between 30 and 60 CV, is used.

After the washing cycles an elution phase is carried out by using a solution like that of the first cycle of washing with an end amount of potassium chloride at a concentration not lower than 10 mM, preferably at a concentration comprised between 15 and 25 mM. An overall amount of solution comprised between 15 and 40 CV, preferably between 20 and 30 CV, is used for the elution.

All the solutions and the sample charged pass through the column at a linear speed comprised between 0.1 and 1 cm/min, preferably between 0.4 and 0.7 cm/min.

Under these conditions rIFNα-2b is eluted from the column with a purity degree higher than 98%, while into the starting solution the purity degree was about 40%, with a yield of recovery of the wanted product higher than 80%.

Figure 1B:
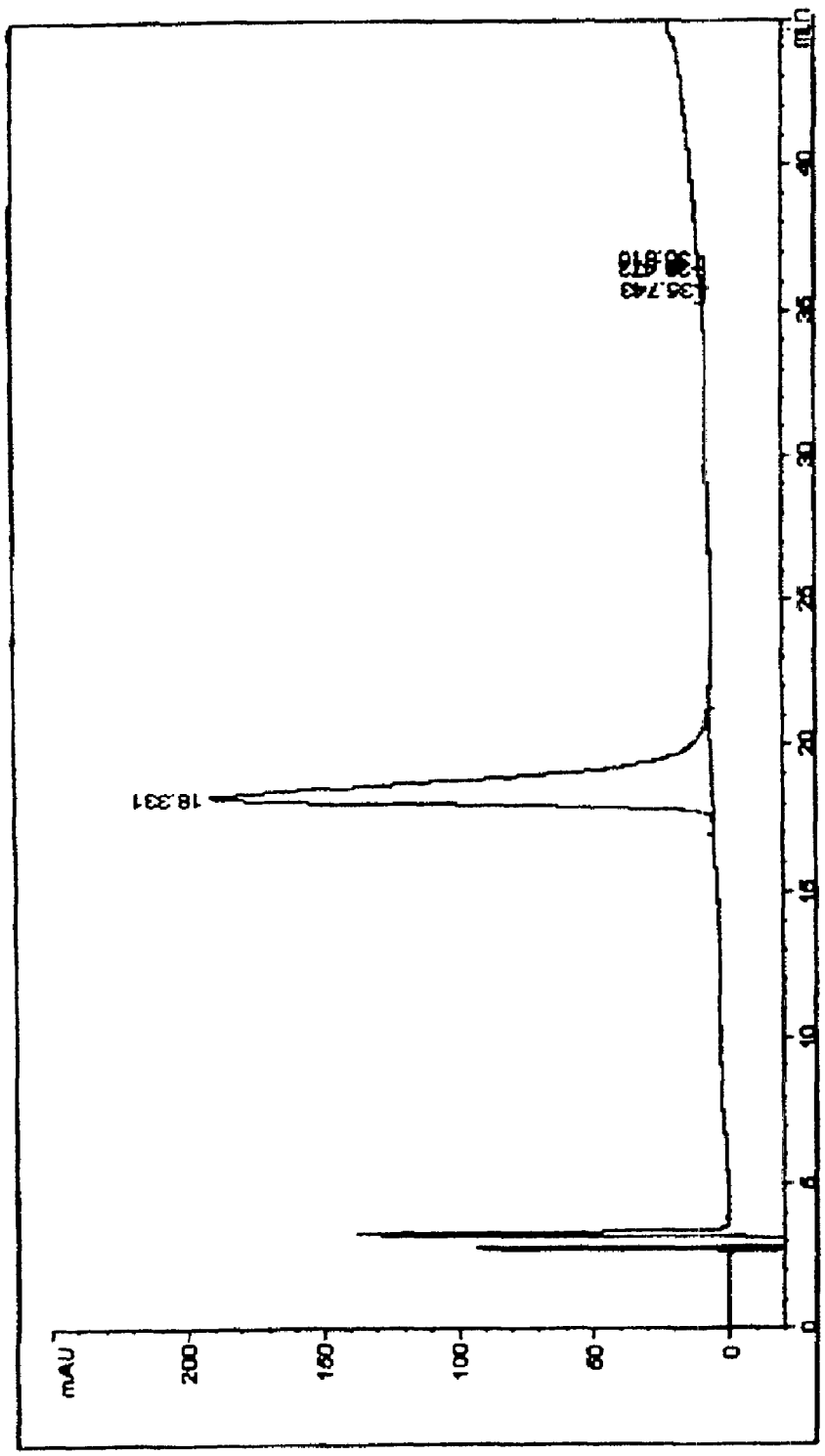

The chromatographic profiles before and after the chromatographic purification are shown in FIGS. 1*a* and 1*b*.

FIG. 1*a* shows the chromatographic profile of the interferon solution before the purification and FIG. 1*b* the chromatographic profile after the purification.

The chromatographic profiles have been carried out in HPLC by means of a liquid chromatograph HP 1090, by using a Vydac C18 column and a UV detector set at 214 nm. The elution has been carried out at a 1 ml/min flow by using a mixture made of two eluents, eluent A made of 700 ml of water, 298 ml of acetonitrile and 2 ml of trifluoroacetic acid and eluent B made of 198 ml of water, 800 ml of acetonitrile and 2 ml of trifluoroacetic acid. The two eluents have been mixed during the elution according to the following table:

| Time (minutes) | % A | % B |
|---|---|---|
| 0 | 72 | 28 |
| 1 | 72 | 28 |
| 5 | 67 | 33 |
| 20 | 63 | 37 |
| 30 | 57 | 43 |

-continued

| Time (minutes) | % A | % B |
|---|---|---|
| 40 | 40 | 60 |
| 42 | 40 | 60 |
| 50 | 28 | 72 |
| 60 | 72 | 28 |

EXAMPLE 3

The process is carried out according to the description of example 2 by using a buffer solution made of monobasic potassium phthalate and sodium hydroxide.

EXAMPLE 4

The process is carried out according to the description of example 2 by using a buffer solution made of dibasic sodium citrate and sodium hydroxide.

EXAMPLE 5

The process is carried out according to the description of example 2 by using a buffer solution made of citric acid and dibasic sodium phosphate.

EXAMPLE 6

The process is carried out according to the description of example 2 by using a buffer solution made of imidazole and hydrochloric acid.

EXAMPLE 7
Purification of Human Serum Albumin

The human serum albumin (HSA) has been purchased from Sigma (catalogue number A1653 of the 2000 year). The nominal title of this albumin preparation is stated 99.6%, but the RP-HPLC analysis shows a real title equal to 88% if the products albumin-like are considered as impurities.

A HSA solution has been prepared in a 20 mM citric acid solution at pH 3 at an end concentration equal to 1 mg/ml and has been charged on a strong cationic exchange column containing chromatographic matrices Mustangs® S (Pall Corporate) commercially available. The cationic exchange column is conditioned before the charge with a 20 mM citric acid solution at pH 3.0 in amounts equal to 20 column volumes (CV).

The amount of the charged solution is such that the value of 10 mg of charged proteins for each milliliter of stationary phase, preferably amounts comprised between 6 and 8 mg/ml, is not exceeded.

After the charge, the products bound to the stationary phase are submitted to the following cycles of washing:

1. washing cycle—40 CV with a 20 mM solution of sodium acetate at pH 5.5;
2. washing cycle—30 CV with a 20 mM solution of sodium acetate at pH 5.8.

The elution of the wanted product from the column is carried out by means of a saline solution at pH 6.0 made of a mixture of monobasic potassium phosphate and dibasic sodium phosphate at a concentration comprised between 5 and 100 mM depending on the composition of the mixture. However the conductivity of the solution has not to exceed 140 µS. A total amount of solution comprised between 25 and 35 CV is used.

All the solutions and the charged sample pass through the column at a linear speed comprised between 0.1 and 1 cm/min, preferably between 0.4 and 0.7 cm/min.

Under these conditions HSA is eluted from the column with a purity higher than 99% with a yield of recovery of the wanted product higher than 56%.

Figure 2A:
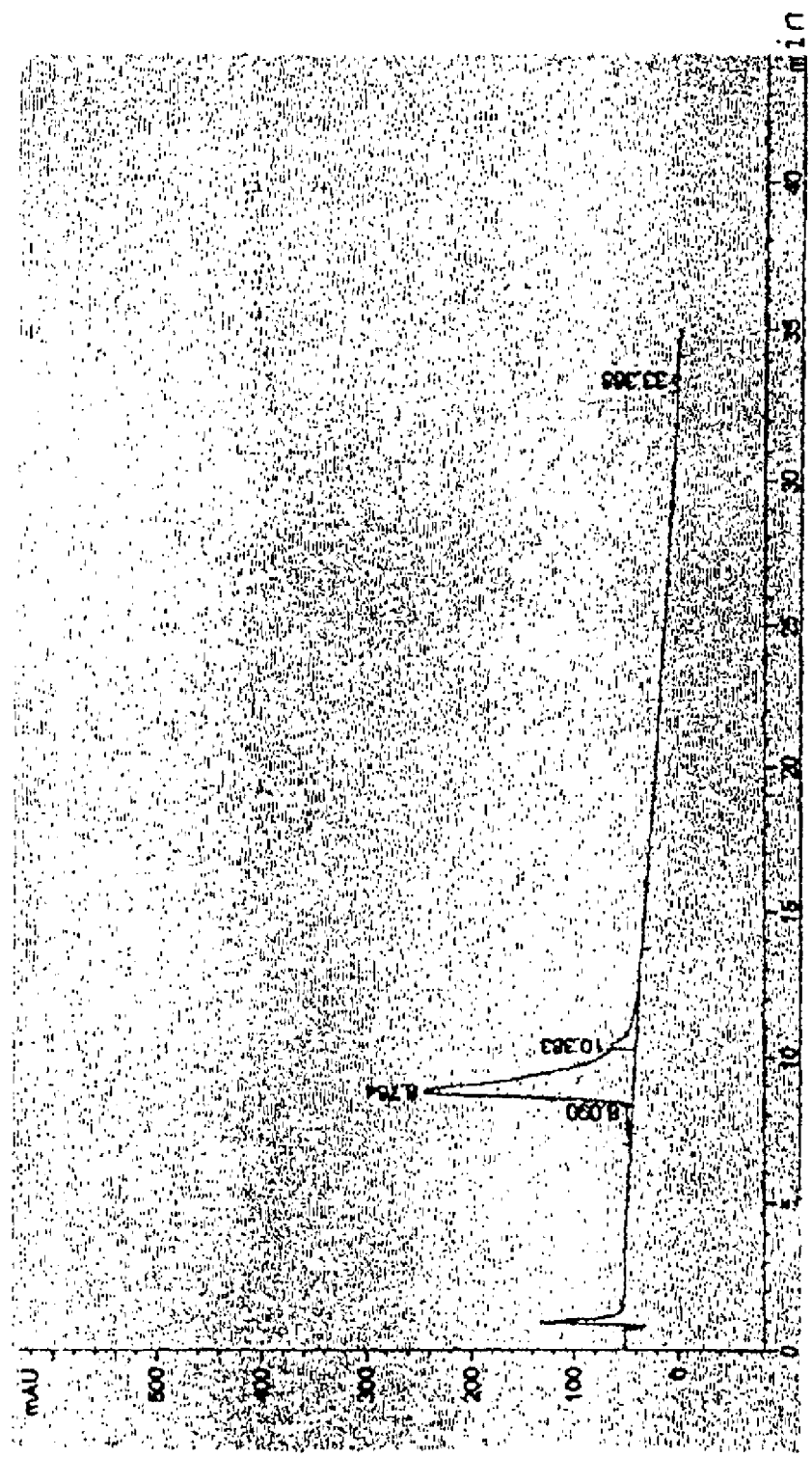
FIGS. 2a and 2b show the HPLC chromatographic profile of HSA before and after the purification.
Figure 2:
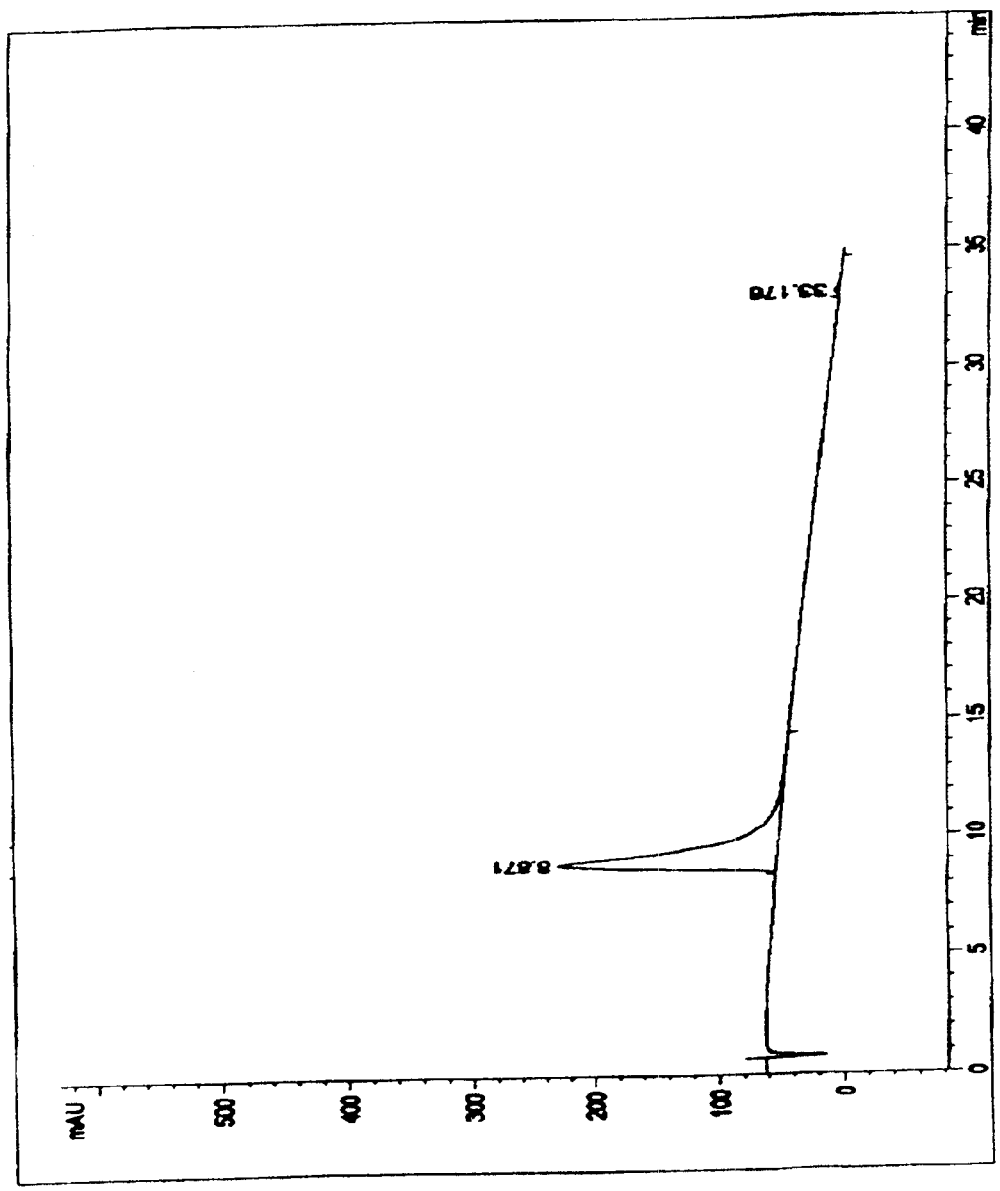

FIGS. 2a and 2b show the HPLC chromatographic profile of HSA before and after the purification. The analysis has been carried out with the same instruments used for FIGS. 1a and 1b by using a mixture of two eluents, eluent A made of 950 ml of 0.1% trifluoroacetic acid and 50 ml of acetonitrile and eluent B made of 950 ml of acetonitrile and 50 ml of 0.1% trifluoroacetic acid. The elution has been carried out with a 1 ml/min flow by using a linear gradient of a mixture of the eluents A and B that starts with 20% of B and arrives to 60% of B in 20 minutes.

What is claimed is:

1. A process for the purification of the recombinant alpha-2b interferon, rIFNα-2b, that comprises charging a proteic mixture coming from the manufacturing by fermentation of the rIFNα-2b added with a 1M solution of sodium acetate and brought to pH 5.5 with acetic acid, on a column filled with strong cationic exchange resin conditioned at pH 5.5 by means of a 20 mM solution of sodium acetate so that between 6 and 8 mg of protein are present for each ml of stationary phase, in submitting the column to two washing cycles, first with a buffer solution at pH 6.1 at a concentration between 5 and 15 mM, then with the same buffer solution added with 2 mM of potassium chloride and lastly in eluting the pure rIFNα-2b from the columns by using a buffer solution at pH 6.1 at a concentration between 5 and 15 mM containing potassium chloride at a concentration comprised between 15 and 25 mM.

2. A process according to claim 1 characterized in that the employed resin is a strong cation exchange medium consisting of a hydrophilic polymer with sulfonic acid groups crosslinked on a poly ether sulfone membrane and the buffer mixtures are selected from those made of monobasic potassium phosphate and dibasic sodium phosphate, monobasic potassium phthalate and sodium hydroxide, dibasic sodium citrate and sodium hydroxide, citric acid and dibasic sodium phosphate, imidazole and hydrochloric acid.

3. A process for the purification of interferon proteins which comprises carrying out a cationic exchange chromatography on a solid matrix at a more basic pH than the pH corresponding to the isoelectric point pI of the interferon proteins to be purified, at which pH said proteins still stay absorbed, and eluting said proteins by increasing the ionic strength and/or the pH of the eluents to achieve a purification of the interferon proteins without hydrophobic interaction chromatography or anionic exchange chromatography.

4. The process according to claim 3, wherein the eluents used in the cationic exchange chromatography are aqueous buffer solutions whose pH is between 2 and 11.

5. The process according to claim 4, wherein the aqueous buffer solutions contain from 5 to 100 mM of the following buffer mixtures: monobasic potassium phosphate and dibasic sodium phosphate, monobasic potassium phthalate and sodium hydroxide, dibasic sodium citrate and sodium hydroxide, citric acid and dibasic sodium phosphate, imidazole and hydrochloric acid.

6. The process according to claim 5, wherein the buffer solutions contain from 1 to 100 mM of organic or inorganic salts apt to modify the ionic strength of the solution.

7. The process according to claim 3, wherein the interferon proteins are alpha, beta, gamma, delta, omega, tau, natural alpha from leukoctyes, recombinant alpha-2b and consensus interferons.

* * * * *